(12) United States Patent
Atkins

(10) Patent No.: US 7,842,844 B2
(45) Date of Patent: Nov. 30, 2010

(54) PROCESS FOR THE CONVERSION OF HYDROCARBONS TO C2-OXYGENATES

(75) Inventor: Martin Philip Atkins, Ashford (GB)

(73) Assignee: BP Chemicals Limited, Middlesex (GB)

( * ) Notice: Subject to any disclaimer, the term of this patent is extended or adjusted under 35 U.S.C. 154(b) by 114 days.

(21) Appl. No.: 11/988,204

(22) PCT Filed: Jun. 29, 2006

(86) PCT No.: PCT/GB2006/002414

§ 371 (c)(1),
(2), (4) Date: Jan. 3, 2008

(87) PCT Pub. No.: WO2007/003897

PCT Pub. Date: Jan. 11, 2007

(65) Prior Publication Data

US 2009/0170963 A1    Jul. 2, 2009

(30) Foreign Application Priority Data

Jul. 6, 2005   (EP) ................... 05254236

(51) Int. Cl.
*C07C 29/14* (2006.01)
*C07C 27/06* (2006.01)

(52) U.S. Cl. .............. 568/880; 568/881; 568/885; 568/910.5

(58) Field of Classification Search .......... 568/880
See application file for complete search history.

(56) References Cited

U.S. PATENT DOCUMENTS

| | | | | |
|---|---|---|---|---|
| 4,348,486 | A * | 9/1982 | Calvin et al. ............. | 518/704 |
| 4,429,056 | A * | 1/1984 | Smith ..................... | 518/700 |
| 4,442,228 | A | 4/1984 | Leupold et al. | |
| 4,670,473 | A * | 6/1987 | Walker et al. ............ | 518/706 |
| 6,284,217 | B1 | 9/2001 | Wang et al. | |
| 6,346,555 | B1 | 2/2002 | Luo et al. | |
| 6,500,781 | B2 * | 12/2002 | Luo et al. ................ | 502/326 |

FOREIGN PATENT DOCUMENTS

| | | |
|---|---|---|
| EP | 0 010 295 A1 | 4/1980 |
| EP | 0 079 132 A1 | 5/1983 |
| EP | 0 303 438 A2 | 2/1989 |
| GB | 2 074 164 | 10/1981 |
| JP | 61/178933 A | 8/1986 |
| JP | 62/148437 A | 7/1987 |
| JP | 62/148438 A | 7/1987 |
| JP | 01/294643 A | 11/1989 |
| WO | WO 99/02254 A1 | 1/1999 |
| WO | WO 00/23689 A1 | 4/2000 |

OTHER PUBLICATIONS

International Search Report for PCT/GB2006/002414 mailed Oct. 10, 2006.
"Hydrocarbon Processing", vol. 78, No. 4, pp. 87-90, 92-93 (Apr. 1999).
"Petrole et Techniques", No. 415, pp. 86-93 (Jul.-Aug. 1998).
"IMRET 3: Proceedings of the Third International Conference on Microreaction Technology"; Editor W. Ehrfeld, Springer Verlag, pp. 187-196 (1999).
"Hydrocarbon Engineering"; vol. 5, No. 5, pp. 67-69 (2000).
"Hydrocarbon Processing", vol. 79, No. 9, p. 34 (Sep. 2000).
"Today's Refinery", vol. 15, No. 8, p. 9 (Aug. 2000).
Weissermel, K., et al; Industrial Organic Chemistry, Second, Revised and Extended Edition, pp. 19-21 (1993).
Translation of Office Action dated Nov. 27, 2009 issued in corresponding Eurasian Patent Application No. 200810171; *Process for the conversion of hydrocarbons to C2-oxygenates*; Applicant: BP Chemicals Limited (1 pg).
Extract of Examination Report issued in corresponding Chinese Patent Application No. 2006800247898 (1 pg).
Gunardson, H.H., et al; "Produce CO-rich synthesis gas"; *Hydrocarbon Processing*, vol. 78, No. 4, pp. 87-90, and 92-93 (Apr. 1999).

(Continued)

*Primary Examiner*—Brian J Davis
(74) *Attorney, Agent, or Firm*—Nixon & Vanderhye

(57) ABSTRACT

Process for the conversion of hydrocarbons to ethanol and optionally acetic acid by converting hydrocarbon in a syngas reactor into a stream A comprising a mixture of carbon oxide (s) and hydrogen preferably having a H2/CO molar ratio between 1.5 and 2.5, converting at least part of stream A in the presence of a particulate catalyst in a reactor under a temperature between 150 and 400° C. and a pressure of 5 to 200 bar, into a C2-oxygenates stream B, where stream B includes water, alkanes, ethanol, acetaldehyde, ethyl acetate and acetic acid, which together represent least 80% by weight of the products obtained from the C2-oxygenates conversion reactor. The C2-oxygenates stream B is separated into a stream C comprising H2, CO, CO2 and alkanes, and a stream D including 15 to 40 wt % of acetic acid, 10 to 40 wt % of acetaldehyde and 15 to 40 wt % of ethanol. At least part of stream D is hydrogenated in a hydrogenation reactor into an ethanol stream E, and stream E is subjected to a separating step, followed by recovery of ethanol.

14 Claims, 2 Drawing Sheets

OTHER PUBLICATIONS

Bourbonneux, G.; "Fisher-Tropsch synthesis gas production routes"; *Petrole et Techniques*, No. 415, pp. 86-93 (Jul.-Aug. 1998).

Mayer, J., et al; "A Microstructured Reactor for the Catalytic Partial Oxidation of methane to Syngas";IMRET 3: *Proceedings of the Third International Conference on Microreaction Technology*; Editor W. Ehrfeld, Springer Verlag, pp. 187-196 (1999).

"Hydrocarbon Engineering"; vol. 5, No. 5, pp. 67-69 (2000).

"Major player invests in GTL technology"; *Hydrocarbon Processing*, vol. 79, No. 9, p. 34 (Sep. 2000).

"Today's Refinery", vol. 15, No. 8, p. 9 (Aug. 2000).

Weissermel, K., et al; "2. Basic Products of Industrial Synthesis";*Industrial Organic Chemistry*, Second, Revised and Extended Edition, pp. 19-21 (1993).

\* cited by examiner

PROCESS FOR THE CONVERSION OF HYDROCARBONS TO C2-OXYGENATES

This application is the U.S. national phase of International Application No. PCT/GB2006/002414 filed 29 Jun. 2006 which designated the U.S. and claims priority to European Patent Application No. 05254236.2 filed 6 Jul. 2005, the entire contents of each of which are hereby incorporated by reference.

The present invention provides a process for the conversion of hydrocarbons to C2-oxygenates in the presence of a particulate catalyst.

In particular, the present invention relates to an improved process for the conversion of hydrocarbons to ethanol and optionally acetic acid in the presence of a particulate rhodium-based catalyst.

BACKGROUND OF THE INVENTION

EP-A-0 010 295 describes a process for preparing ethanol from synthesis gas, in which the reaction is carried out over a supported rhodium catalyst comprising, as cocatalyst, one or more of the elements zirconium, hafnium, lanthanum, platinum, chromium and mercury.

EP-A-0 079 132 relates to a process for preparing oxygenated hydrocarbons by catalytic reaction of synthesis gas over a supported catalyst comprising, as active components, rhodium, silver, zirconium and molybdenum and also, if desired, iron, manganese, rhenium, tungsten, ruthenium, chromium, thorium and potassium. The preferred support material is silicon dioxide.

JP 62/148437 and JP 62/148438 disclose the simultaneous production of acetic acid, acetaldehyde and ethanol from a synthesis gas reacted in the presence of a rhodium catalyst pretreated with sulfur-containing compounds. JP 61/178,933 discloses producing oxygenates from a synthesis gas wherein the reaction is carried out in the presence of a rhodium catalyst provided with an accelerator metal such as scandium, iridium or an alkali earth metal. JP01/294643 discloses the production of oxygenated compounds such as acetic acid in which a synthesis gas is reacted in the presence of a rhodium catalyst on a silica substrate.

U.S. Pat. No. 6,346,555 and U.S. Pat. No. 6,500,781 disclose a catalyst and a process for preparing C2-oxygenates by reaction of CO and H2 over a rhodium-containing supported catalyst, in which the catalyst consists essentially of rhodium, zirconium, iridium, at least one metal selected from amongst copper, cobalt, nickel, manganese, iron, ruthenium and molybdenum, and at least one alkali metal or alkaline earth metal selected from amongst lithium, sodium, potassium, rubidium, magnesium and calcium, on an inert support.

SUMMARY OF THE INVENTION

Figure 1:
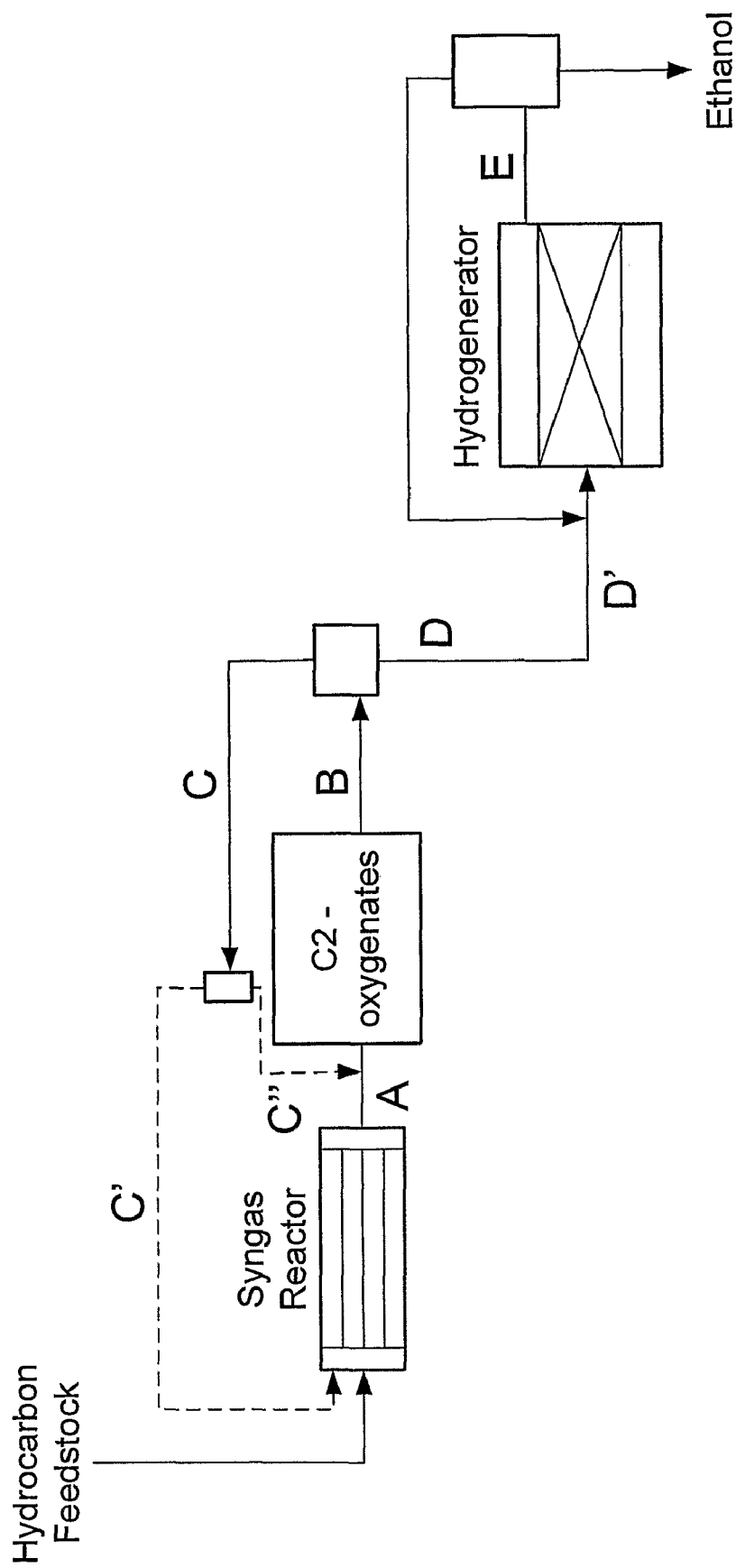
FIGS. 1 and 2 represent embodiments of a process scheme according to the present invention. These said embodiments comprise optional and/or preferred process steps according to the present invention. The letter references in these Figures correspond to those used in the present description and appending claims.
Figure 2:
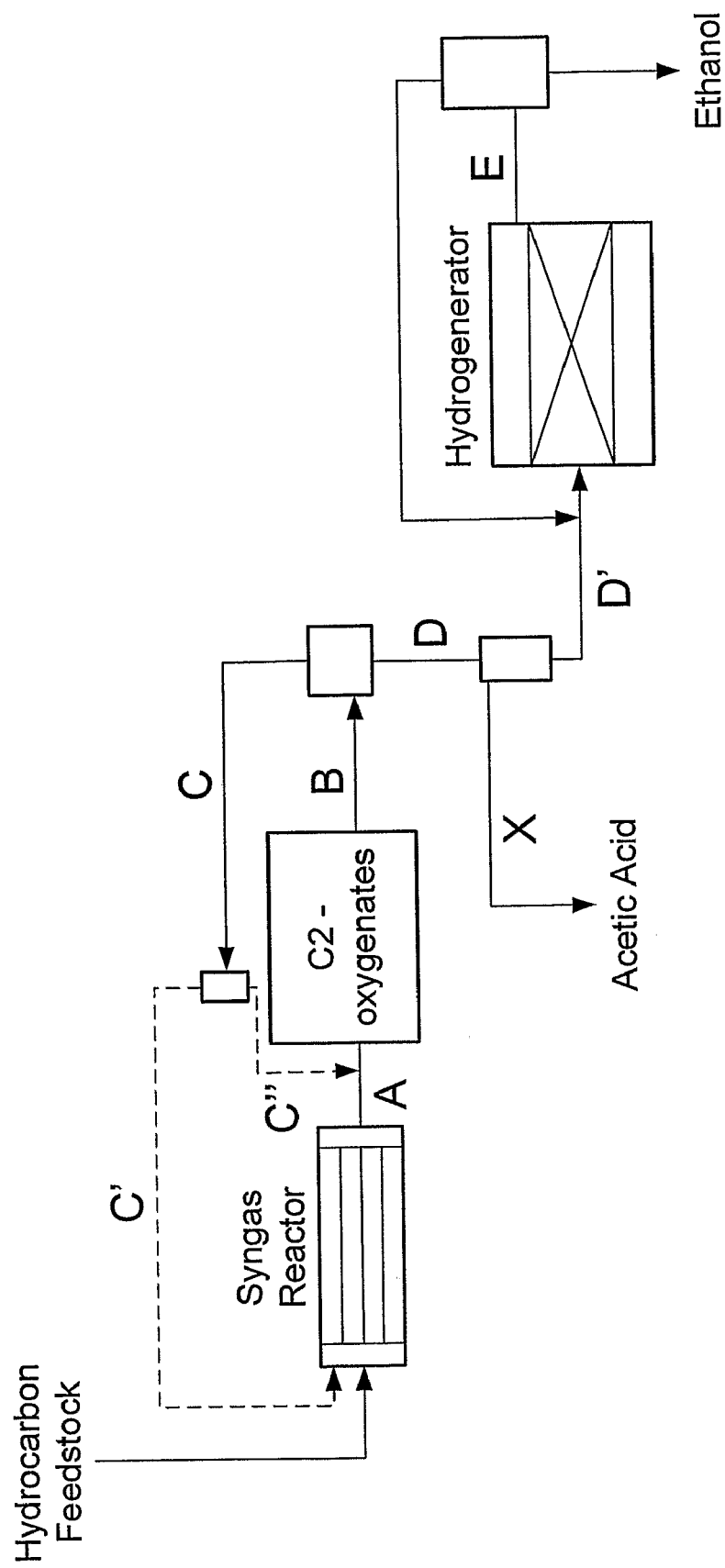

According to the present invention, a process is provided for the conversion of hydrocarbons to ethanol and optionally acetic acid comprising the steps of:

1. converting hydrocarbon in a syngas reactor into a stream A, consisting of a mixture of carbon oxide(s) and hydrogen, preferably having a H2/CO molar ratio comprised between 1.5 and 2.5,
2. converting at least part of stream A in the presence of a particulate catalyst in a reactor under a temperature comprised between 150 and 400° C. and a pressure of 5 to 200 bar, into a C2-oxygenates stream B,
3. separating the C2-oxygenates stream B into a stream C comprising H2, CO, CO2 and alkanes, and a stream D comprising the C2-oxygenates,
4. optionally separating the stream D into an acetic acid stream X and a C2-oxygenates stream D',
5. hydrogenating stream D, or optional stream D', in an hydrogenation reactor into an ethanol stream E, and
6. subjecting stream E to a separating step and recovering ethanol.

In particular, the present invention relates to an improved process in terms of selectivity and catalyst activity and operating life for the conversion of hydrocarbons to ethanol and optionally acetic acid in the presence of a particulate rhodium-based catalyst, said conversion proceeding via a syngas generation intermediate step.

According to an embodiment of the present invention, the C2-oxygenates are mainly ethanol, acetaldehyde, ethyl acetate and acetic acid; said ethanol, acetaldehyde, ethyl acetate and acetic acid preferably represent together at least 40% by weight of the products obtained from the C2-oxygenates conversion reactor, more preferably at least 50% by weight, and most preferably at least 60% by weight.

According to an embodiment of the present invention, water and alkanes (stream B) are also produced in the C2-oxygenates conversion reactor; then, water, alkanes (essentially methane and ethane), ethanol, acetaldehyde, ethyl acetate and acetic acid preferably represent together at least 80% by weight of the products obtained from the C2-oxygenates conversion reactor (stream B), more preferably at least 90% by weight, most preferably at least 95% by weight.

The C2-oxygenates feed then preferably comprises about 15 to 40% by weight of acetic acid, about 10 to 40% by weight of acetaldehyde and about 15 to 40% by weight of ethanol.

According to the present invention, the C2-oxygenates stream B is separated into a stream C comprising H2, CO, CO2 and alkanes, and a stream D comprising essentially the C2-oxygenates. According to a preferred embodiment of the present invention, this separation is performed by using distillation column(s).

According to an embodiment of the present invention, at least part of stream C can be recycled back to the syngas reactor. According to another embodiment of the present invention, at least part of stream C is then separated into the alkanes (C') and the syngas (C''), the alkanes being preferably recycled into the syngas reactor and the syngas being preferably recycled into the C2-oxygenates conversion reactor together with the stream A. According to a preferred embodiment of the present invention, this separation is performed by using distillation column(s).

According to an optional embodiment of the present invention, stream D is separated into an acetic acid stream X and a C2-oxygenates stream D'. This can be done in a "flash" distillation in which most of the acetaldehyde and ethanol (stream D') is flashed overhead with some of the water, and the remaining acetic acid is left at the bottom (stream X) of the column (along with water). The said bottom stream contains approximately 90% by weight of the acetic acid and about 90% by weight of the water from the crude products, i.e. a bottom stream composition that represents about 50% by weight of the total crude product(s). The said separation preferably takes place by using a splitter column. The acetic acid stream is then preferably subjected to a drying step in order to recover dry acetic acid, which subsequently can be sold on the acetic acid market.

According to the present invention stream D, or optional stream D', are hydrogenated in a hydrogenation reactor into an ethanol stream E. This can be done by using conventional hydrogenation process conditions. The Applicants have unexpectedly found that, by proceeding with the hydrogenation of the feed D (or optional D') under conventional hydrogenation conditions, the selectivity to ethanol reached unexpected levels. Whilst not wishing to be bound by this theory, the Applicants believe that the high selectivity is due to the particular mixture of chemicals present in the process, i.e. the mixture of (acids), aldehydes, esters and alcohols favour ethanol production.

According to the present invention, stream E is subjected to a separation step and ethanol is recovered. This final separation step can be performed, for example, by using distillation column(s) or Zeolite processing.

The particulate catalyst used in the C2-oxygenates reactor according to the present invention is preferably a rhodium catalyst. Preferably, the rhodium catalyst used in the present invention is a rhodium catalyst supported on a micro-porous silica, said micro-porous silica preferably having a BET specific surface area of 150 to 350 m2/g, preferably 150 to 349 m2/g, and most preferably 200 to 300 m2/g, an average pore size of 100 to 300 Å, preferably 101 to 300 Å, and most preferably 150 to 250 Å and a pore volume of 0.5 to 1.5 ml/g, and most preferably 0.9 to 1.1 ml/g.

The BET surface area, average pore size and pore volume have been obtained by Micromeritics ASAP 2010 and N2 adsorption-desorption techniques.

Preferably, the rhodium catalyst used in the present invention is a rhodium catalyst supported on a micro-porous silica, consisting of components Rh—Mn—Fe-M1-M2 wherein M1 can be Li and/or Na and M2 can be Ru and/or Ir, wherein Rh is 0.1 to 3%, preferably 0.3 to 2%, by weight (based on the total catalyst weight) and the weight ratio of Mn/Rh is 0.5-12, the weight ratio of Fe/Rh is 0.01-0.5, the weight ratio of M1/Rh is 0.04-0.2, and the weight ratio of M2/Rh is 0.1-1.0.

Processes for producing mixtures of carbon monoxide and hydrogen (synthesis gas) are well known. Each has its advantages and disadvantages and the choice of using a particular reforming process is dictated by: economics; available feed stream considerations; as well as by the desired mole ratio of H2:CO in the feedstock resulting from the reforming reaction. The synthesis gas may be prepared using any of the processes known in the art including partial oxidation of hydrocarbons, steam reforming, gas heated reforming, microchannel reforming (as described in, for example, U.S. Pat. No. 6,284,217 which is herein incorporated by reference), plasma reforming, autothermal reforming and any combination thereof. A discussion of these synthesis gas production technologies is provided in "Hydrocarbon Processing" V78, N. 4, 87-90, 92-93 (April 1999) and "Petrole et Techniques", N. 415, 86-93 (July-August 1998). It is also envisaged that the synthesis gas may be obtained by catalytic partial oxidation of hydrocarbons in a microstructured reactor as exemplified in "IMRET 3: Proceedings of the Third International Conference on Microreaction Technology", Editor W Ehrfeld, Springer Verlag, 1999, pages 187-196. Alternatively, the synthesis gas may be obtained by short contact time catalytic partial oxidation of hydrocarbonaceous feedstocks as described in EP 0303438. Preferably, the synthesis gas is obtained via a "Compact Reformer" process as described in "Hydrocarbon Engineering", 2000, 5, (5), 67-69; "Hydrocarbon Processing", 79/9, 34 (September 2000); "Today's Refinery", 15/8, 9 (August 2000); WO 99/02254; and WO 200023689.

Any hydrocarbon-containing feed stream that can be converted into a feedstock comprising carbon monoxide and hydrogen, most preferably a synthesis gas (or "syngas"), is useful in the processes of the present invention. The ratio of hydrogen to carbon monoxide in the reaction zone is preferably in the range of 20:1 to 0.1:1 by volume, more preferably in the range of 5:1 to 1:1, and most preferably in the range of 2.5:1 to 1.5:1, e.g. 2:1. Useful feed streams include natural gas (mainly methane, but natural gas composition can vary depending on location and source), naphtha, refinery off-gas, LPG, gas oil, vacuum residuals, shale oils, asphalts, various types of fuel oils, coal based/lignin deposits and hydrocarbon containing process recycle streams. According to a preferred embodiment of the present invention, methane is used as the hydrocarbon-containing feed stream to be converted into CO and H2.

Feedstocks comprising carbon monoxide and hydrogen, e.g., synthesis gas, may undergo purification prior to being fed into any of the reaction zones of the present invention. For use in the processes of the present invention, the synthesis gas should ideally be predominantly free of any catalyst poisons and inhibitors, such as hydrogen sulfide, carbonyl sulfide, metal carbonyls, e.g., iron carbonyl and nickel carbonyl, ammonia, basic organic compounds, e.g., methyl amine and ethyl amine, and generally any compounds that will neutralize an acid. Synthesis gas purification may be carried out by processes known in the art. See, for example, Weissermel, K. and Arpe H.-J., Industrial Organic Chemistry, Second, Revised and Extended Edition, 1993, pp. 19-21.

The particular reaction conditions for the C2-oxygenates conversion reactor are not narrowly critical, and may be any effective reaction conditions sufficient to produce mainly oxygen containing hydrocarbon compounds. The exact reaction conditions implemented in the said process, will ultimately be governed by the best compromise between achieving high catalyst selectivity, activity and lifetime, whilst continuing to maintain overall ease of operability. Further considerations for the intrinsic reactivity of the starting materials in question, and the stability of the said starting materials and the desired reaction product to the reaction conditions will also be made when deciding upon the exact conditions of the present invention.

In one embodiment of this invention, feedstock comprising the desired molar ratio of H2:CO is fed into the C2-oxygenates conversion reactor at a controlled rate, and the reaction is carried out in a reaction zone under controlled temperature and pressure conditions, in the presence of a catalyst in order to convert the feedstock into oxygenates. The temperature in the reaction zone is selected from the range of from about 150° C. to about 400° C., preferably a temperature in the range of from about 200° C. to about 350° C. The gas hourly space velocity (GHSV) of the feedstock (liters of feedstock/hr/liter of catalyst) passing through the reaction zone can vary significantly, depending upon a variety of factors such as, for example, reaction conditions, composition of the feedstock and quantity and type of catalyst being used. The GHSV can be maintained at any rate in the range of from about 1 to about 30,000 hr−1 or more, preferably will be maintained at a rate of at least about 500 hr−1, and more preferably will be maintained at a rate of at least 1,000 hr−1. The pressure in the C2-oxygenates conversion reactor zone may be selected from the range of from about 5 to 200 bar, preferably a pressure in the range of from about 25 to 120 bar. The hydrogen and carbon monoxide partial pressures should be sufficient to enable the production of oxygenates. Hydrogen and carbon monoxide may be fed separately to the conversion reactor or, preferably in combination, e.g., as synthesis gas.

For purposes of this invention, GHSV is gas hourly space velocity which is the rate of gas flow over the catalyst. It is determined by dividing the volume of gas (at 25° C. and 1 atmosphere) which passes over the catalyst in one hour by the volume of the catalyst. LHSV, is liquid hourly space velocity, which is the rate that the liquid organic substrate is fed to the conversion reactor. It is determined by dividing the liquid volume pumped in one hour by the volume of catalyst present.

The conversion to oxygenates reaction can be carried out by passing the mixture of hydrogen and carbon monoxide over the rhodium-based catalyst as a vapor phase reaction or as a liquid phase reaction, e.g., slurry reaction.

The reaction may be carried out in any appropriate reactor, e.g. a tubular reactor using a fixed bed of the catalyst. The reactants may be fed to the catalyst by feeding down or up, or a combination of both, to a fixed bed located in a tubular reactor. It may be desirable, but not restrictive, to use a reactor design that operates by plug flow and causes minimal turbulence in the reactor zone. The reaction may be effected in a dynamic bed of the catalyst. In such a reaction, the catalyst bed is moving in the same manner as seen with a fluid bed of catalyst.

The invention claimed is:

1. Process for the conversion of hydrocarbons to ethanol and acetic acid comprising the steps of:
   i. converting hydrocarbon in a syngas reactor into a stream A comprising a mixture of carbon oxide(s) and hydrogen,
   ii. converting at least part of stream A in the presence of a particulate catalyst in a reactor under a temperature comprised between 150 and 400° C. and a pressure of 5 to 200 bar, into a C2-oxygenates stream B, where stream B includes water, alkanes, ethanol, acetaldehyde, ethyl acetate and acetic acid, which together represent least 80% by weight of the products obtained from the C2-oxygenates conversion reactor,
   iii. separating the C2-oxygenates stream B into a stream C comprising $H_2$, CO, $CO_2$ and alkanes, and a stream D including 15 to 40 wt % of acetic acid, 10 to 40 wt % of acetaldehyde and 15 to 40 wt % of ethanol,
   iv. hydrogenating at least part of stream D in an hydrogenation reactor into an ethanol stream E, and
   v. subjecting stream E to a separating step and recovering ethanol.

2. Process according to claim 1 wherein the particulate catalyst used in step ii is a rhodium-based catalyst.

3. Process according to claim 1 wherein the C2-oxygenates comprise ethanol, acetaldehyde, ethyl acetate and acetic acid; and said ethanol, acetaldehyde, ethyl acetate and acetic acid preferably represent together at least 40% by weight of the products obtained from the C2-oxygenates conversion reactor.

4. Process according to claim 1 wherein water, alkanes, ethanol, acetaldehyde, ethyl acetate and acetic acid represent together at least 90% by weight of the products obtained from the C2-oxygenates conversion reactor (stream B).

5. Process according to claim 1 wherein at least part of stream C is recycled back to the syngas reactor.

6. Process according to claim 1 wherein at least part of stream C is then separated into the alkanes (C') and the syngas (C").

7. Process according to claim 1, including the step of separating the stream D into an acetic acid stream X and a C2-oxygenates stream D'.

8. Process according to claim 3 wherein said ethanol, acetaldehyde, ethyl acetate and acetic acid represent together at least 50% by weight of the products obtained from the C2-oxygenates conversion reactor.

9. Process according to claim 3 wherein said ethanol, acetaldehyde, ethyl acetate and acetic acid represent together at least 60% by weight of the products obtained from the C2-oxygenates conversion reactor.

10. Process according to claim 1 wherein water, alkanes, ethanol, acetaldehyde, ethyl acetate and acetic acid represent together at least 95% by weight of the products obtained from the C2-oxygenates conversion reactor.

11. Process according to claim 6 wherein all of stream C is separated into the alkanes (C') and the syngas (C").

12. Process according to claim 6 wherein the alkanes are recycled into the syngas reactor.

13. Process according to claim 1 wherein the syngas is recycled into the C2-oxygenates conversion reactor together with the stream A.

14. Process according to claim 1, wherein stream A comprises a mixture of carbon oxide(s) and hydrogen having a $H_2$/CO molar ratio between 1.5 and 2.5.

* * * * *